United States Patent [19]
Hori et al.

[11] Patent Number: 4,611,928
[45] Date of Patent: Sep. 16, 1986

[54] METHOD FOR MEASURING COAGULATION OF MILK

[75] Inventors: Tomoshige Hori, Kitamoto; Masatoshi Kako, Sayama; Hayashi Hiromichi, Tokyo, all of Japan

[73] Assignee: Snow Brand Milk Products Co., Ltd., Japan

[21] Appl. No.: 693,998

[22] PCT Filed: May 25, 1984

[86] PCT No.: PCT/JP84/00269
§ 371 Date: Jan. 23, 1985
§ 102(e) Date: Jan. 23, 1985

[87] PCT Pub. No.: WO84/04813
PCT Pub. Date: Dec. 6, 1984

[30] Foreign Application Priority Data
May 25, 1983 [JP] Japan ................................. 58-92079

[51] Int. Cl.⁴ ...................... G01N 25/18; G01R 27/07
[52] U.S. Cl. ........................................ 374/21; 73/64.1; 324/65 P

[58] Field of Search ..................... 374/21, 16; 73/64.1, 73/54

[56] References Cited
U.S. PATENT DOCUMENTS 3,453,864 7/1969 Chiu ....................................... 374/21
3,821,643 6/1974 Bostick et al. .................... 73/64.1 X
3,840,806 10/1974 Stoner et al. ..................... 324/65 R
4,059,006 11/1977 Mizutani et al. ....................... 374/21

FOREIGN PATENT DOCUMENTS

0437964 2/1973 U.S.S.R. .............................. 73/64.1

Primary Examiner—Daniel M. Yasich
Attorney, Agent, or Firm—McGlew and Tuttle

[57] ABSTRACT

A measurement method for determining the state of coagulation of raw milk in a production process for, for example, cheese or yogurt. According to this method, the state of coagulation of milk can be determined by placing a metal wire in the milk and, while feeding an electric current continuously or intermittently to the metal wire, measuring the temperature of the metal wire over a given period of time.

3 Claims, 8 Drawing Figures

METHOD FOR MEASURING COAGULATION OF MILK

TECHNICAL FIELD

This invention relates to a measurement method for determining the state of coagulation of raw milk in production processes of, for example, cheese and yogurt, and more specifically to a measurement method for thermally determining property changes which accompany the coagulation of milk.

The term "milk" as used herein means raw milks used primarily for the production of cheese and yogurt, such as whole milk, skimmed milk and reconstituted milk.

BACKGROUND ART

The coagulation stage of milk is the most important and fundamental treatment step in, for example, the production of cheese. The state of coagulation essentially governs the quality of the resulting final product. Given these circumstances, the determination of the state of coagulation of milk has conventionally been carried out subjectively on the basis of the experience of skilled technicians. On the other hand, a number of measurement methods have also been invented to measure the coagulation of milk by means of instruments. However these methods are accompanied by such drawbacks as the milk coagulum has to be squeezed or pressed to cause it to change shape, and in some instances, cause whey to be released. As a result, measurements are made on the coagulated milk in a state different from its normal state. Use of such measurement methods are thus limited to research purposes, and they are impractical for actual application in the production of, for example, cheese.

DISCLOSURE OF THE INVENTION

Given the above-described situation, the present inventors have conducted an investigation with a view toward developing a method for measuring the coagulation of milk, which method may be applied to the production process of, for example, cheese. As a result, it has been found that the state of coagulation of milk can be determined by thermally investigating property changes which accompany the coagulation of milk.

Accordingly, an object of this invention is to provide a method for measuring the coagulation of milk, which method is capable of determining the state of coagulation without the need to apply external pressure such as squeezing or pressing to the milk coagulum and can be applied to the production process of, for example, cheese.

A special feature of the constitution of this invention resides in that in the coagulation stage of milk, the state of coagulation is determined by placing a metal wire in the milk and then measuring with time the temperature of the metal wire while feeding an electric current either intermittently or continuously to the metal wire.

BEST MODE FOR CARRYING OUT THE INVENTION

The metal wire to be placed in milk in the present invention should have a diameter of 0.01 mm–2 mm or so and is preferably made of platinum. In order to place such a metal wire into milk (raw milk) to be coagulated and then to cause a current to pass therethrough, the method exemplified in FIGS. 1 and 2 of the accompanying drawings should be followed.

Figure 1:
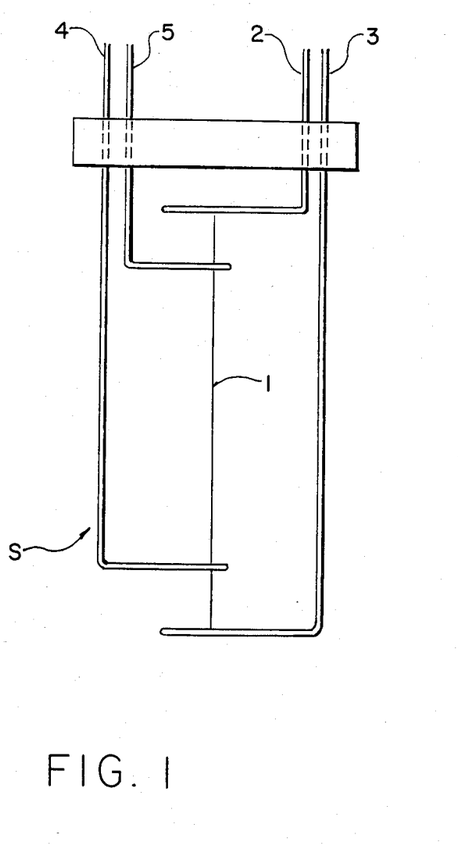
FIG. 1 exemplifies a sensor which consists of a metal wire to be employed for measurements in the present invention.
Figure 2:
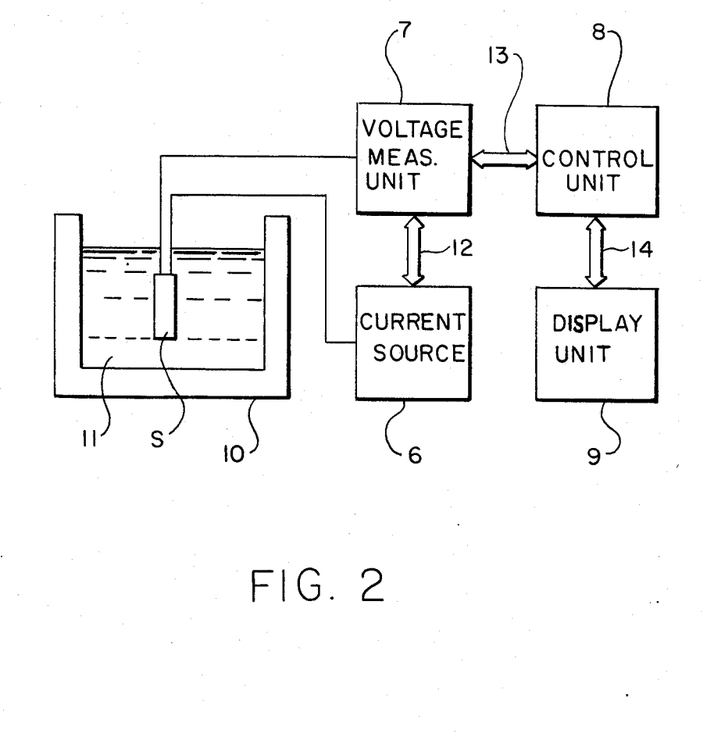
FIG. 2 exemplifies the manner for using the sensor to measure the coagulation of milk.

In FIG. 1, 1 indicates a platinum wire. Current-feeding terminals 2,3 are connected to the two ends of the platinum wire, whereas voltage-measuring terminals 4,5 are connected at suitable preselected locations on the platinum wire, preferably at locations apart by 1 cm or more from their corresponding terminals 2,3. The thus-assembled unit, which is generally designated S in FIG. 1, is used as a measuring sensor in this invention along with a voltage measuring unit 7 which is shown in FIG. 2. FIG. 2 exemplifies the manner for using the above measuring sensor to measure the coagulation of milk. In the Figure, there are illustrated the sensor S, a current source (constant electric current source) 6, a voltage-measuring unit 7, a control unit 8, a display unit 9 for time vs. temperature curves, a coagulation vat 10 for milk, raw milk 11 and a conventional control system 12–14.

In the above-described embodiment of this invention, the sensor S is placed in the raw milk (for example, skimmed milk) held in the vat 10 and while feeding a current (usually, a direct and constant electric current) either intermittently or continuously from the current source 6 to the sensor, temperature variations of the metal wire, which variations occur due to coagulation of the raw milk, are measured over a given period of time. This measurement of temperature variations is effected by measuring the voltage of the metal wire by means of the voltage-measuring unit 7, and the temperature variations are calculated in accordance with the following equation:

$$\theta = (V/iR_o - 1)/\alpha$$

where $\theta$ means the temperature (°C.) of the metal wire, V the voltage (in volts) of the metal wire, i the electric current (in amps) of the metal wire, $R_o$ the electrical resistance ($\Omega$) of the metal wire at 0° C., and $\alpha$ the temperature coefficient (1/° C.) of the electrical resistance.

Determination of the state of coagulation of the raw milk can then be carried out by measuring the display 9 of a logarithmic time vs. temperature curve (in the case of intermittent electric current feeding) or a time vs.

temperature curve (in the case of continuous electric current feeding) for the metal wire while feeding a current to the metal wire in the above-described manner. It is quite clear that the wire 1 with its terminals 4, 5 and the voltage measuring unit 7 act as a temperature measuring structure. The same wire 1 is heated over terminals 2,3 and current source 6. Display 9 gives the temperature over a period of time (see FIG. 3).

Figure 3:
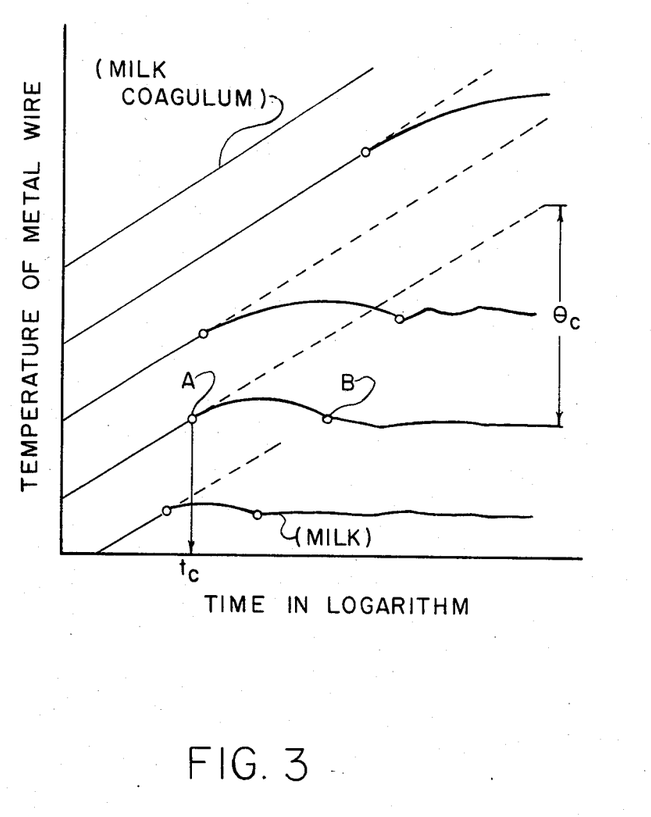
FIGS. 3 and 4 show the relationship between the temperature of the metal wire and the time, when a direct and constant electric current was fed intermittently and continuously to the metal wire, respectively.
Figure 4:
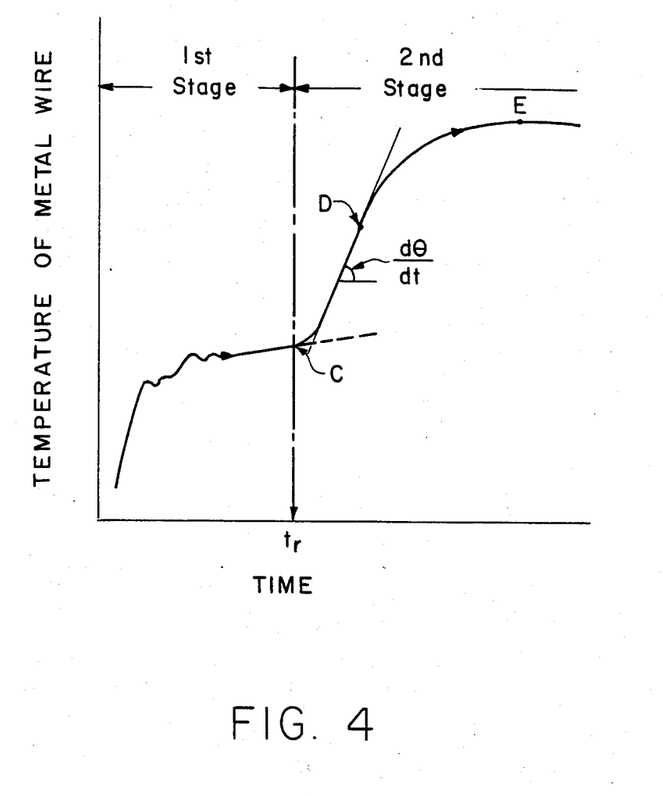

The relationship between the temperature variations of the metal wire and logarithmic time and between the temperature variations and time are shown in FIG. 3 (in the case of intermittent electric current feeding) and FIG. 4 (in the case of continuous electric current feeding). respectively.

As can be seen in FIG. 3, convection occurs around the metal wire after point A. Thus, the mechanism of heat transfer from the fine metal wire toward the surrounding raw milk changes from conduction heat transfer to convection neat transfer. The time of point A, i.e., the convection-producing time (tc), becomes gradually longer as the coagulation of the raw milk proceeds owing to treatment by, for example, rennet added to the raw milk. On the other hand, the degree of temperature drop $\theta c$ of the metal wire, which temperature drop takes place in association with the occurrence of convection, becomes conversely less. Further, after point B, nonsteady-state convection, i.e., turbulence occurs.

When rennet is added to raw milk to cause it to coagulate, characteristic changes can be observed, as shown in FIG. 4, in the change from an enzymatic reaction (1st stage) to a non-enzymatic changes (2nd stage) and in the elapsed change in the 2nd stage. These changes in the 2nd stage show the state of coagulation of the raw milk. It may be mentioned that $\kappa$ (kappa)-casein (which takes part in the stabilization of casein micelle in milk protein) which is locally present on the surface of casein micelle of the raw milk is specifically degraded by chymosin contained in rennet in the 1st stage. In the 2nd stage, the casein micelle, the hydrophobicity of which has increased due to the degradation of $\kappa$-casein, reacts with calcium ions, thereby inducing coagulation of casein micelle and coagulating the raw milk.

The electric current to be fed to the metal wire in the present invention is determined in accordance with the diameter of the metal wire. In the case of platinum wires having diameters of 0.03 mm and 0.1 mm, for example, direct and constant electric currents of 0.05–0.2 A and 0.5–1.0 A, respectively, are preferred.

No special limitation is imposed on the length of each metal wire. However, to obtain measurement accuracy, about 5–30 cm is preferred.

As has been described above, the state of coagulation of raw milk can be determined by detecting variations in the hydrodynamic characteristics of the milk, which variations occur in association with the coagulation of the milk, while feeding an elecric current to a metal wire placed in the milk, primarily by detecting variations in kinematic viscosity as variations in the transfer of heat from the metal wire heated because of the feeding of the electric current thereto to the surrounding milk.

When a direct and constant electric current is fed to a metal wire, for example, a platinum wire placed in raw milk, the temperature of the metal wire rises because of Joule heat. However, this temperature increase does not give any problem or inconvenience in conducting measurements in accordance with this invention, because its rise is limited. In other words, when the surrounding milk is heated by the thus-heated metal wire, differences occur in the density of the milk and convection is soon produced. Since the quantity of heat carried away by heat transfer through convection will increase in proportion to the temperature of the thus-heated metal wire, the temperature of the metal wire will reach an equilibrium value at a certain time point as long as the milk is present in a sufficient amount when a direct and constant electric current is fed continuously. Since the influence of radiation can be ignored in the above case, the transfer of heat from the metal wire to the surrounding milk is effected by means of conduction and convection. When milk is subjected to a coagulation treatment, the proportions of transfer of heat by means of conduction and of convection in the transfer of heat are not constant over a given period of time. Since the kinematic viscosity increases as the coagulation proceeds, the proportion of the transfer of heat by convection decreases correspondingly.

Further explanation will be made in this matter. When a metal wire placed in a liquid is one-step heated (heated not gradually but instantaneously), heat is transferred from the metal wire to the surrounding fluid by means of conduction alone during the time immediately following the heating (for example, 5 seconds when a direct and constant electric current of 0.7 A is fed to a platinum wire of 0.1 mm in diameter and 10.8 cm long fixed vertically in reconstituted skimmed milk having an total solid content of 10% and a temperature of 30° C.). As a result, as theoretically derived from Fourier equation of heat conduction, the temperature of the metal wire increases linearly relative to logarithmic time. When the temperature of the metal wire however rises further and exceeds a certain critical value, convection will be produced around the metal wire (point A in FIG. 3) and thereafter hydrodynamic effects will become dominant. In other words, the velocity of heat transfer will become greater because of the effects of the transfer of heat by means of convection. Therefore, the rate of temperature increase of the metal wire will be reduced correspondingly, and the transfer of heat will then be changed to the transfer of heat by turbulence which is non-periodic convection (point B in FIG. 3), thereby allowing the temperature of the metal wire to reach substantially an equilibrium value. Since the time span from one-step heating to the occurrence of convection increases gradually as the coagulation of milk proceeds, it is possible to measure the coagulation of the milk by observing the convection-producing time to or the degree of the temperature drop $\theta c$ of the metal wire due to convection over a given period of time while feeding a direct and constant current intermittently to the metal wire in the course of the coagulation treatment of the milk.

On the other hand, when a direct and constant electric current is fed continuously to the metal wire, the coagulation of the milk can be measured as variations in the equilibrium temperature of the metal wire over a given period of time. In other words, when the kinematic velocity increases and the proportion of the transfer of heat by means of convection in the heat transfer decreases along with the progress of coagulation of the milk as mentioned above, the equilibrium temperature of the metal wire will rise significantly, leading to provision of the characteristic time vs. temperature curve shown in FIG. 4.

Among the methods of this invention, according to the method featuring the continuous feeding of a current to a metal wire, it is feasible not only to measure the coagulation of milk in a qualitative fashion, but also to determine the milk-coagulating capacity of rennet from the length tr of the 1st stage in FIG. 4 when the coagulation treatment of milk is effected using rennet. The milk-coagulating capacity of rennet varies in a complicated pattern, depending, for example, on the type and concentration of the rennet, the conditions of the milk and the treatment temperature. In addition, the velocity at which milk coagulates has a major effect on the texture of cheese and can also be estimated as a relative value from the rate of temperature variation in the 2nd phase of FIG. 4 (for example, the gradient $d\theta/dt$ of the curve at point D). On the analogy of heat transfer, the kinematic viscosity of the milk coagulum can also be immediately obtained from the degree of temperature increase of the metal wire. By feeding a direct and constant electric current continuously to the metal wire during the rennet treatment of milk, it is possible to measure, from the characteristic curve of FIG. 4, the entire process of the milk coagulation in a continuous, quantitative and non-destructive manner. Further, the completion of the coagulation can be determined from point E, at which the temperature of the metal wire becomes constant relative to the time.

As mentioned above, the present invention permits precise determination of the state of coagulation by thermally measuring changes in the characteristic properties of raw milk, which changes occur along with the coagulation, on the basis of temperature changes in a metal wire placed in the raw milk over a given period of time when an electric current is fed to the metal wire. Accordingly, the present invention can solve the drawbacks mentioned above which are encountered in conventional experience-dependent judgements or in instrument-dependent measurements used in laboratories.

According to the present invention, it is also possible to measure some parameters which pertain to the hydrodynamic characteristics which accompany the coagulation of raw milk. It is thus possible to determine without fail a very soft coagulation state (for example, the coagulation of yogurt) which has hitherto been considered difficult to determine.

The sensor used for measurement in this invention is in principle composed of a single piece of metal wire. It thus has such advantages as, even when used in an actual production process, it is free from the problems involved with conventional instruments in washing and because the physical quantity actually measured is the voltage of the metal wire, it can be used directly as a signal for automatic control of the rennet treatment of milk.

The present invention will be described in further detail by the following Examples:

EXAMPLE 1

Placed in a cylindrical flask 8.4 cm in diameter and 18 cm high was a sample which had been prepared by adding 0.03% of rennet to 1 liter of reconstituted skimmed milk having an total solid content of 10% and a temperature of 30° C. Along the central axis of the flask, a platinum wire ($R_o = 1.3974$ Ω; $\alpha = 3.817 \times 10^{-3}$ 1/° C.) 0.1 mm in diameter and 10.8 cm long was placed and fixed.

Figure 5:
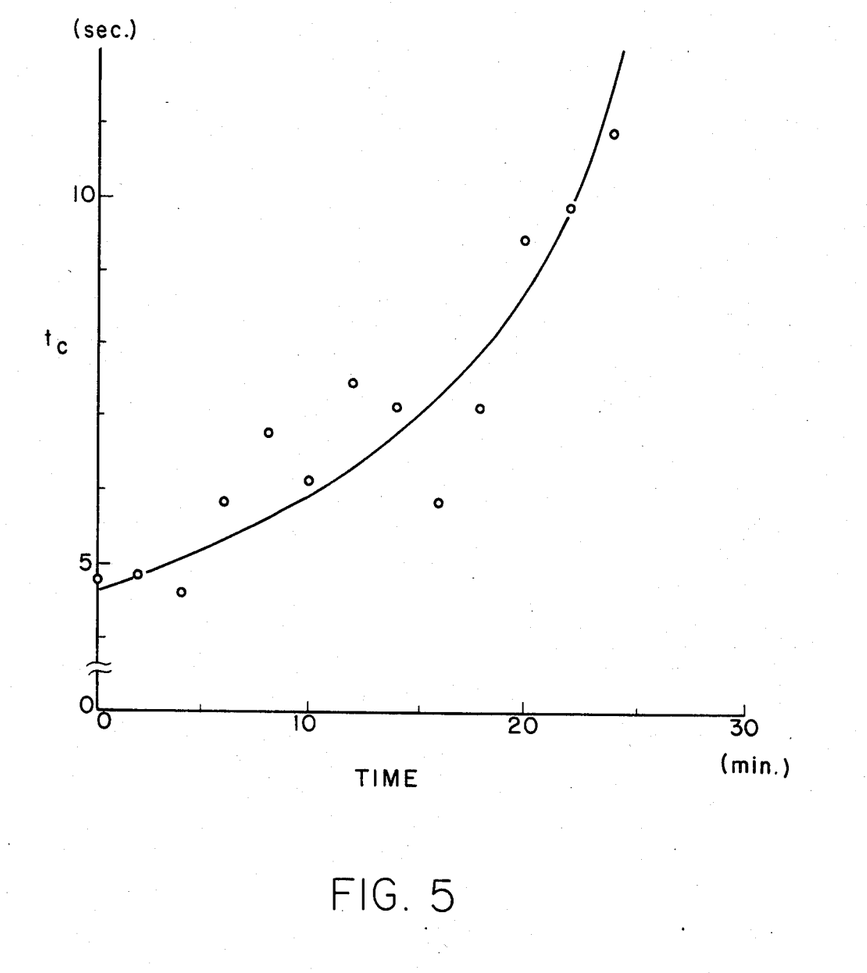
FIGS. 5 and 6 illustrate the convection-starting time (tc) in raw milk and the degree of temperature drop ($\theta c$), respectively, due to convection when a direct and constant electric current was intermittently fed in Example 1 of this invention.
Figure 6:
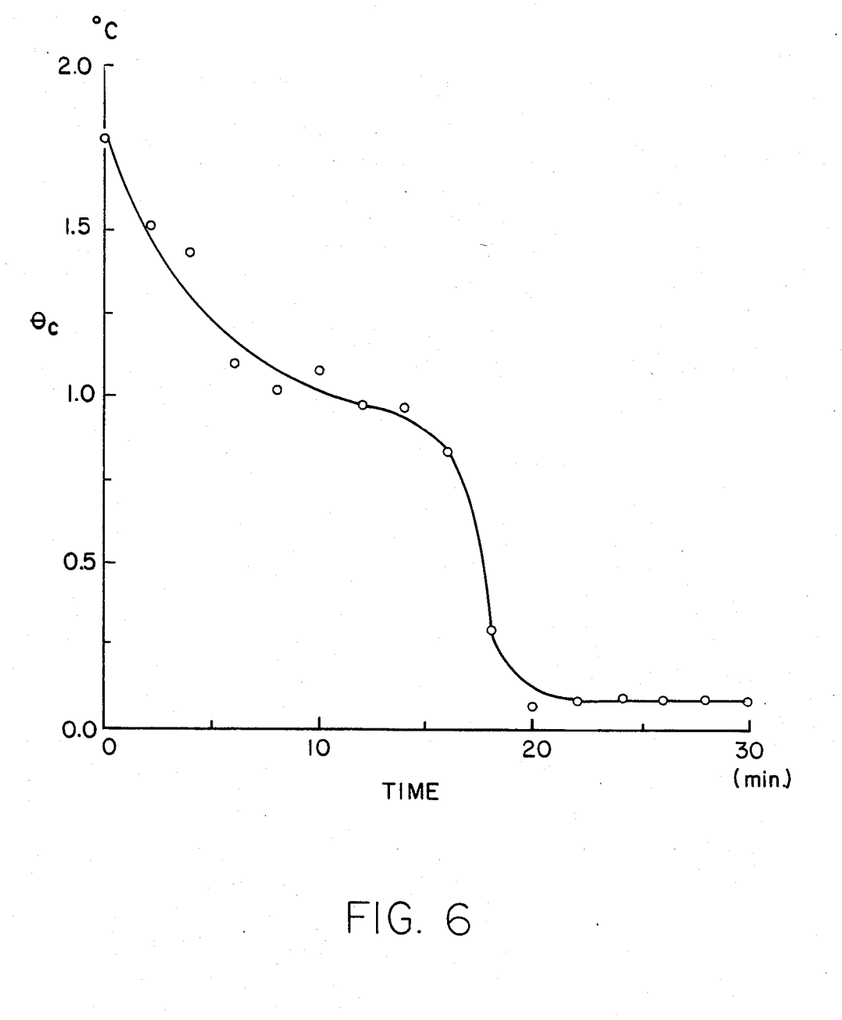

Then, a direct and constant electric current of 0.7 A was fed intermittently for 1 minute every 5 minutes after the addition of rennet to the platinum wire to obtain a logarithmic time vs. temperature curve. When the convection-producing time tc and the degree of temperature drop $\theta c$ due to the convection (30 seconds after the feeding of the current), corresponding to point A in FIG. 3, were measured, the tc increased significantly and the $\theta c$ decreased significantly as the coagulation of the reconstituted skim milk proceeded (see FIGS. 5 and 6 where the circles show actual experimental points through which the curves shown can be generated).

Figure 7:
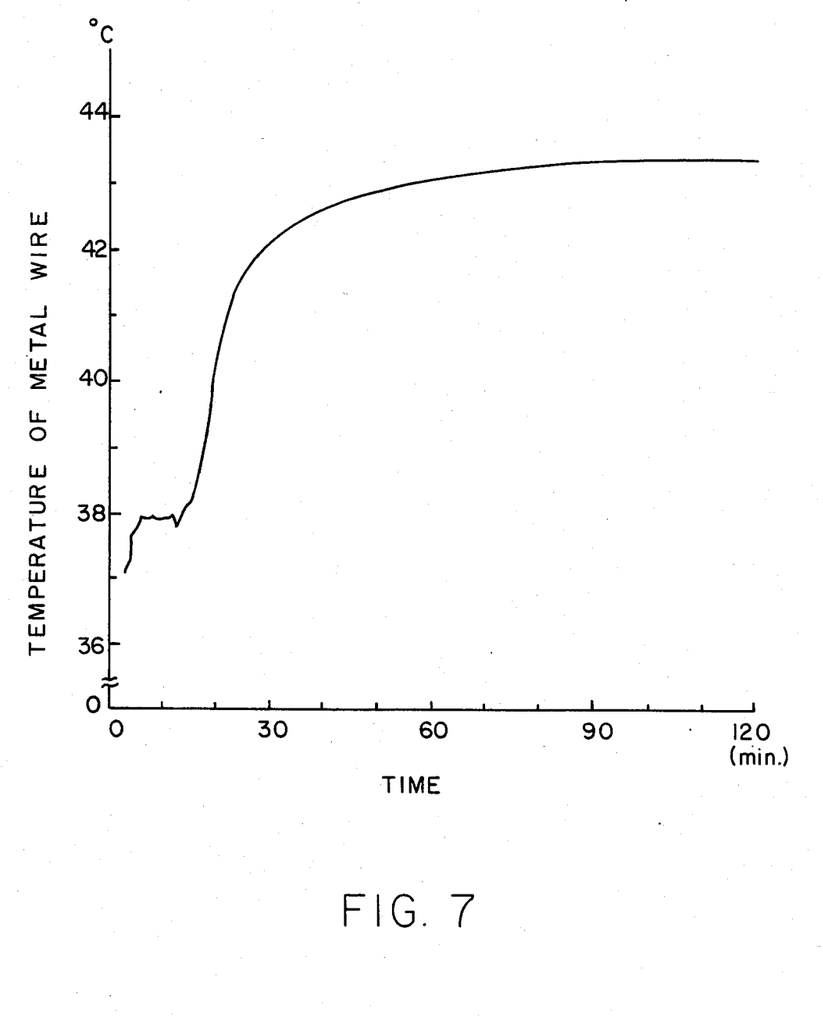
FIG. 7 shows the time dependence of the temperature of the metal wire when a direct and constant electric current was also fed continuously.

Using the same sample, a direct and constant electric current of 0.7 A was continuously fed to obtain the characteristic curve shown in FIG. 4. It was able to measure, in about 20 minutes after the addition of rennet, the state of change from the 1st stage, i.e., the enzymatic reaction, to the 2nd stage, i.e., the coagulation of casein micelle (see FIG. 7). Separately, a characteristic curve was also determined on a sample as a control which did not have rennet added. Changes characteristic to the coagulation of milk were not observed.

EXAMPLE 2

Figure 8:
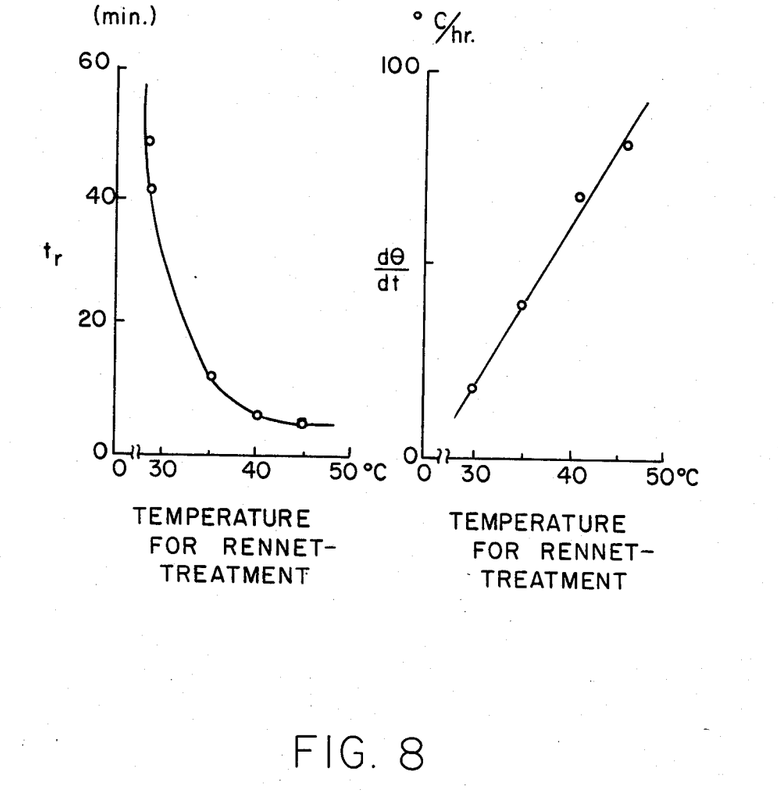
FIG. 8 illustrates the relationship among the length (tr) of the 1st stage, the coagulating velocity ($d\theta/dt$) of raw milk and the treatment temperature when a direct and constant electric current was continuously fed in Example 2.

Using a sample which had been obtained by adding 0.09% of rennet to 1 liter of reconstituted skim milk having an total solid content of 8.5% and a temperature of 30° C.–45° C., an electric current was continuously fed under the same conditions as those employed in Example 1 to determine the length (tr, min.) of the 1st stage and the coagulation velocity (the gradient $d\theta/dt$, °C./hr. at point D in FIG. 4). As a result, the time tr required for the reaction in the 1st stage decreased exponentially as the temperature of the rennet treatment rose and substantially reached equilibrium at 40° C. On the other hand, the temperature-rising velocity $d\theta/dt$ which is considered to correspond to the coagulation speed increased linearly relative to the treatment temperature (see FIG. 8). The findings resulting from these measurements conformed with findings experienced in connection with changes in the properties of milk due to rennet treatment.

Although each of the above Examples relates to coagulation by rennet, measurement can be made in the same manner when coagulation is effected by using a microorganism rennet (for example, *Mucor pusillus*).

We claim:

1. A measurement method for determining the state of coagulation of milk in production processes of milk products such as cheese and yogurt, which method comprises placing, as a measuring sensor, an assembled probe unit for insertion in the milk consisting of a metal wire having a preselected length, current-feeding terminals and voltage-measuring terminals connected to preselected spaced locations on said metal wire, selectively supplying an electric current either intermittently or continuously through the metal wire and, while the electric current is being supplied therethrough, measuring and recording the degree of temperature increase of the metal wire through the measuring sensor over a given period of time thereby determining the state of coagulation of the milk in a continuous, quantitative and non-destructive manner.

2. A measurement method as claimed in claim 1, wherein said assembled unit, as a measuring sensor, is composed of a metal wire, the current-feeding terminals connected to two ends of the metal wire and the voltage-measuring terminals selectively connected to two other locations of the metal wire.

3. A measuring method, as claimed in claim 2, including adding rennet to the milk to cause it to coagulate during the continuous supply of electric current.

* * * * *